United States Patent [19]
Tajima et al.

[11] Patent Number: 5,682,232
[45] Date of Patent: Oct. 28, 1997

[54] MICROPLATE LIGHT-OBSTRUCTION DEVICE AND LIGHT-EMISSION MEASURING APPARATUS

[75] Inventors: Hideji Tajima; Nobuo Nagaoka, both of Inagi; Minoru Ogasawara; Mitsunao Tanaka, both of Tokyo, all of Japan

[73] Assignees: Precision System Science Co., Ltd.; Iatron Laboratories, Inc., both of Tokyo, Japan

[21] Appl. No.: 699,588

[22] Filed: Aug. 19, 1996

[30] Foreign Application Priority Data

Aug. 25, 1995 [JP] Japan .................................. 7-238936

[51] Int. Cl.⁶ .................................................. G01N 21/76
[52] U.S. Cl. .......................... 356/246; 250/361 C; 422/52
[58] Field of Search ................................ 356/246, 244, 356/440; 422/52; 250/361 C

[56] References Cited

U.S. PATENT DOCUMENTS

| | | | |
|---|---|---|---|
| 4,349,510 | 9/1982 | Kolehmainen et al. | 356/244 |
| 5,290,513 | 3/1994 | Berthold et al. | 250/361 C |

FOREIGN PATENT DOCUMENTS

| | | |
|---|---|---|
| 5157699 | 6/1993 | Japan . |
| 5209830 | 8/1993 | Japan . |
| 5281143 | 10/1993 | Japan . |
| 783831 | 3/1995 | Japan . |

*Primary Examiner*—Richard A. Rosenberger
*Attorney, Agent, or Firm*—Jordan and Hamburg

[57] ABSTRACT

A light-emission measuring apparatus which is capable of eliminating various secondary problems in addition to shutting off strong light from the external and preventing crosstalk. The light-emission measuring apparatus is equipped with a box-type carrier 9 having an open top surface and made to accommodate a microplate 7 comprising a plurality of wells. The box-type carrier is disposed to be movable horizontally. A light-obstruction plate having a light-receiving hole 11 is disposed above the box-type carrier to be movable vertically. The light-obstruction plate 5 is brought into tight contact with a circumference of the box-type carrier 9 to establish a black box when being moved downwardly. Further, the light-receiving hole 11 of the light-obstruction plate 5 has a cylindrical projecting bottom surface 12 so that its bottom surface side outer circumference comes into tight contact with a circumference 13 of an opening of a well top surface of the microplate 7.

5 Claims, 3 Drawing Sheets

MICROPLATE LIGHT-OBSTRUCTION DEVICE AND LIGHT-EMISSION MEASURING APPARATUS

BACKGROUND OF THE INVENTION

1. Field of the Invention

The present invention relates to a light-emission measuring apparatus for a non-returnable container, called a microplate, comprising a plurality of wells, which has come into widespread use as a container for measurement of a sample or a specimen such as a biological component.

2. Description of the Prior Art

Recently, as a high-sensitivity measuring method for biological components or the like, there has been widely used a light-emission measuring method of measuring an amount of extremely weak light such as bioluminescence and chemiluminescence by means of a high-sensitivity light-receiver such as a photomultiplier. Even in the case of the aforesaid microplate being used as a measured-sample container, this light-emission measuring method is being introduced thereinto, and some have already been known as light-emission measuring apparatus for the microplate.

Such apparatus are required to resolve two problems: to completely shut off strong or intensive light from the external and to measure a quantity of extremely weak light a sample emits; and to block stray light from adjacent different wells to prevent the occurrence of so-called crosstalk.

Countermeasures against these problems have been disclosed by Japanese Unexamined Patent Publication Nos. 5-157699, 5-209830, 5-281143, and 7-83831.

Of these, Japanese Unexamined Patent Publication Nos. 5-157699, 5-281143 and 7-83831 all relate to a structure in which a cylindrical light-obstruction member or a light-receiving opening (inlet) of a light-receiving device moves up and down. For light obstruction, during measurement the cylindrical light-obstruction member or the light-receiving opening moves downwardly to be brought into contact with or put in the top surface of a given well of a microplate.

In the case of mere contact therewith, this takes effects to avoid the crosstalk while difficulty is encountered to sufficiently shut off the strong light from the external because a slight gap may take place therebetween due to dimension error caused by the variations in microplate from different makers or due to processing accuracy, particularly its surface condition or surface cuts. For this reason, there is a need for a double obstruction construction in order to further protect the entire apparatus against the leakage of light.

In this case, the light-obstruction for the entire apparatus signifies that the apparatus gets into an airtight condition, with the result that a long-term use causes the temperature within the apparatus to abnormally increase owing to the heat generated from motors and electronic parts installed therein. Particularly, immune reactions and enzyme reactions generally take place at measurement of biological components, and hence it is desirable that the temperature of the microplate itself is regulated to approximately 37° C. However, in the case of such an apparatus, when the temperature within the apparatus exceeds 37° C., the temperature control becomes impossible with no provision of a cooling unit. In addition, mounting the cooling unit results in increase in size of the apparatus concurrent with increase in its manufacturing cost.

Moreover, in the case of the cylindrical light-obstruction member or the light-receiving opening bottom surface being fitted in the top surface of the microplate, there is a need to use a microplate with a high processing accuracy particularly designed and manufactured for the apparatus. The microplate is basically disposable, and the method for use and the kind of the microplate depend upon the object being measured. Thus, the important thing is that it is available anywhere coupled with being low in cost and fit for general purpose. Applying further structural burdens to the microplate side impairs the performance of the entire apparatus and thus leads to a severe disadvantage.

On the other hand, in a radiation measuring apparatus disclosed in Japanese Unexamined Patent Publication No. 5-209830, a throttle plate having at least one restriction hole is stationarily placed between a radiation detector and a microplate so that the microplate is inserted into a bottom surface of the throttle plate under a constant pressure and is horizontally movable. In the case of such a method, its construction becomes simple to offer an advantage in cost, while the ability to shut off the strong light from the external is insufficient, which requires the double light-obstruction construction. What is worse, since the whole top surface of the microplate always slides on the bottom surface of the throttle plate during its movement, if the sample liquid or the like is scattered on the microplate top surface, it can spread to many other wells with a considerable probability, thus causing cross-contamination.

As described above, although being subjected to various improvements for the obstruction of the strong light from the external and the crosstalk prevention, the prior light-emission measuring apparatus for a microplate still do not reach completion in structure and thus newly create secondary problems such as the temperature control of the microplate, the limitation to particularly designed and manufactured microplates and the cross-contamination.

SUMMARY OF THE INVENTION

It is therefore an object of the present invention to eliminate various secondary problems as well as to remove the problems on the obstruction of the strong light from the external and on the crosstalk prevention. For elimination of the aforesaid problems, in accordance with the present invention, a microplate light-obstruction device is equipped with a box-type carrier having an open top surface and made to accommodate a microplate comprising a plurality of wells and disposed to be movable horizontally, and further equipped with a light-obstruction plate having a light-receiving hole and disposed above the box-type carrier to be movable vertically so that the light-obstruction plate is brought into tight contact with the circumference of the box-type carrier when being moved downwardly to establish a black box, the light-receiving hole of the light-obstruction plate having a cylindrical projecting bottom surface so that its bottom surface side outer circumference comes into tight contact with a circumference of an opening section of the well top surface of the microplate (claim 1).

Furthermore, in accordance with this invention, a light-emission measuring apparatus utilizes the above-described microplate light-obstruction device, and a recessed guide hole is made around the light-receiving hole in the light-obstruction plate top surface, and further a nozzle fixing block having a through-hole made coaxially with respect to the light-receiving hole is placed above the guide hole so that a nozzle of a trigger reagent injector faces the through-hole, the guide hole of the light-obstruction plate being made to be slidable when the light-obstruction plate moves up and down with respect to the nozzle fixing block and a light-emission detecting means being located above the through-hole (claim 3). Or, a through-hole is made coaxially with respect to the light-receiving hole and a nozzle fixing block which makes a nozzle of a trigger reagent injector face the through-hole is disposed above the light-receiving hole, and an elastic light-obstruction member such as a bellows is provided for envelopment so that the light-obstruction plate is movable up and down, to thus shut off the light from the external through a gap between the light-receiving hole of the light-obstruction plate and the through-hole of the nozzle fixing block, and further a light-emission detecting means being situated above the through-hole (claim 4). The combination of both the structures is also possible (claim 5).

The microplate light-obstruction device and light-emission measuring apparatus based thereon according to this invention take a double light-obstruction construction, while the outside light-obstruction method for shutting off the strong light from the external is engineered to hermetically seal only the microplate-accommodating box-type carrier but not the entire system and thus the heat generated from motors or electronic parts can be dispersed and discharged to the outside of the system through the natural convection or a fan. Accordingly, the microplate is unaffected by the heat therefrom, with the result that the temperature control with a high accuracy is possible with no use of a cooling unit.

In addition, since the box-type carrier can completely shut off the strong light from the external, the crosstalk prevention is sufficiently accomplished only in such a way that the microplate top surface merely comes into contact with the light-receiving hole outer circumference, and hence there is no need to prepare a microplate particularly designed and manufactured. Besides, since the light-obstruction plate retreats upwardly during the movement of the microplate, the cross contamination is avoidable.

BRIEF DESCRIPTION OF THE DRAWINGS

The object and features of the present invention will become more readily apparent from the following detailed description of the preferred embodiments taken in conjunction with the accompanying drawings in which.

DETAILED DESCRIPTION OF THE INVENTION

Figure 1:
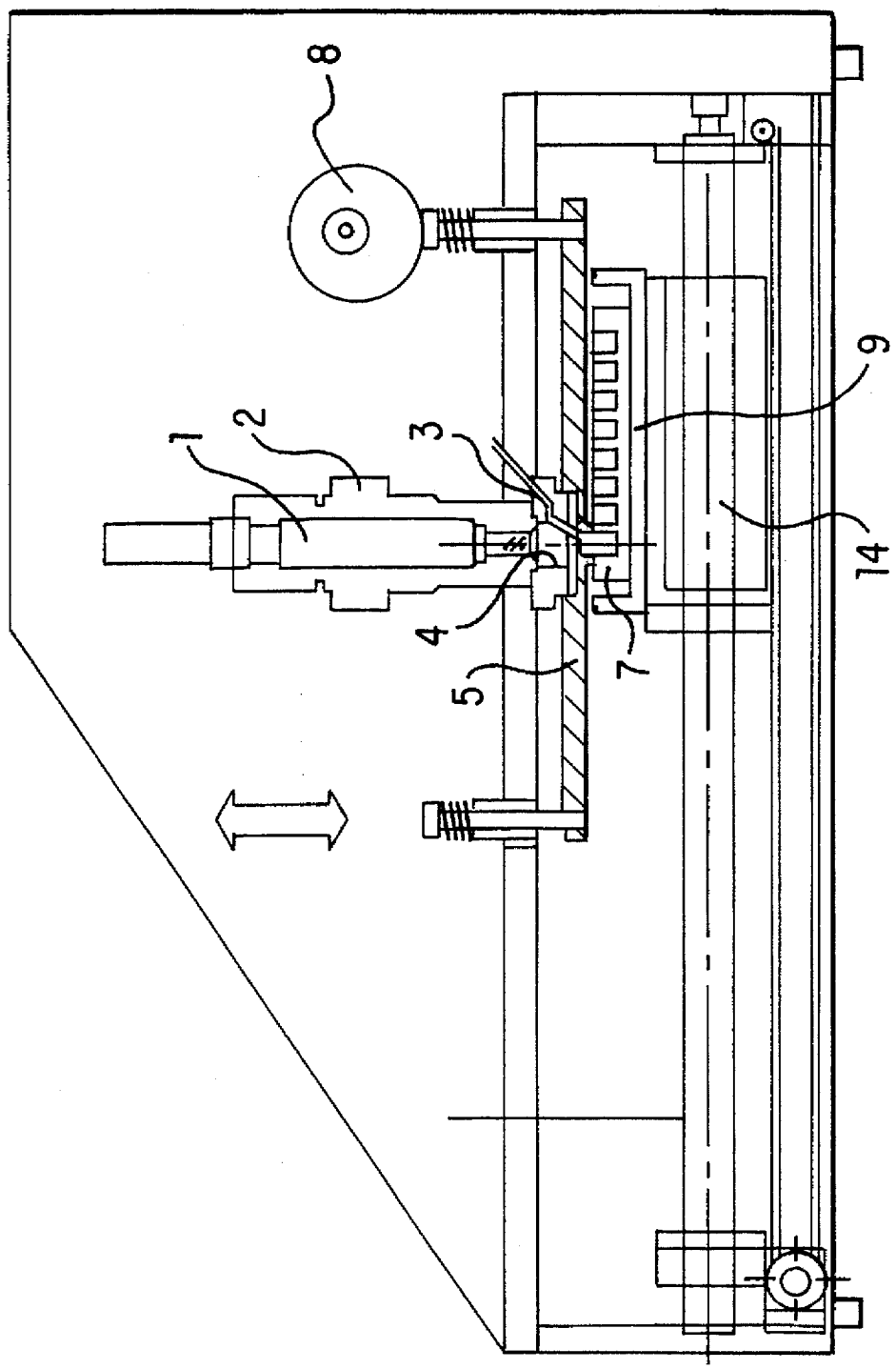
FIG. 1 is a cross-sectional view showing a light-emission measuring apparatus according to an embodiment of the present invention which is in a measuring condition.
Figure 2:
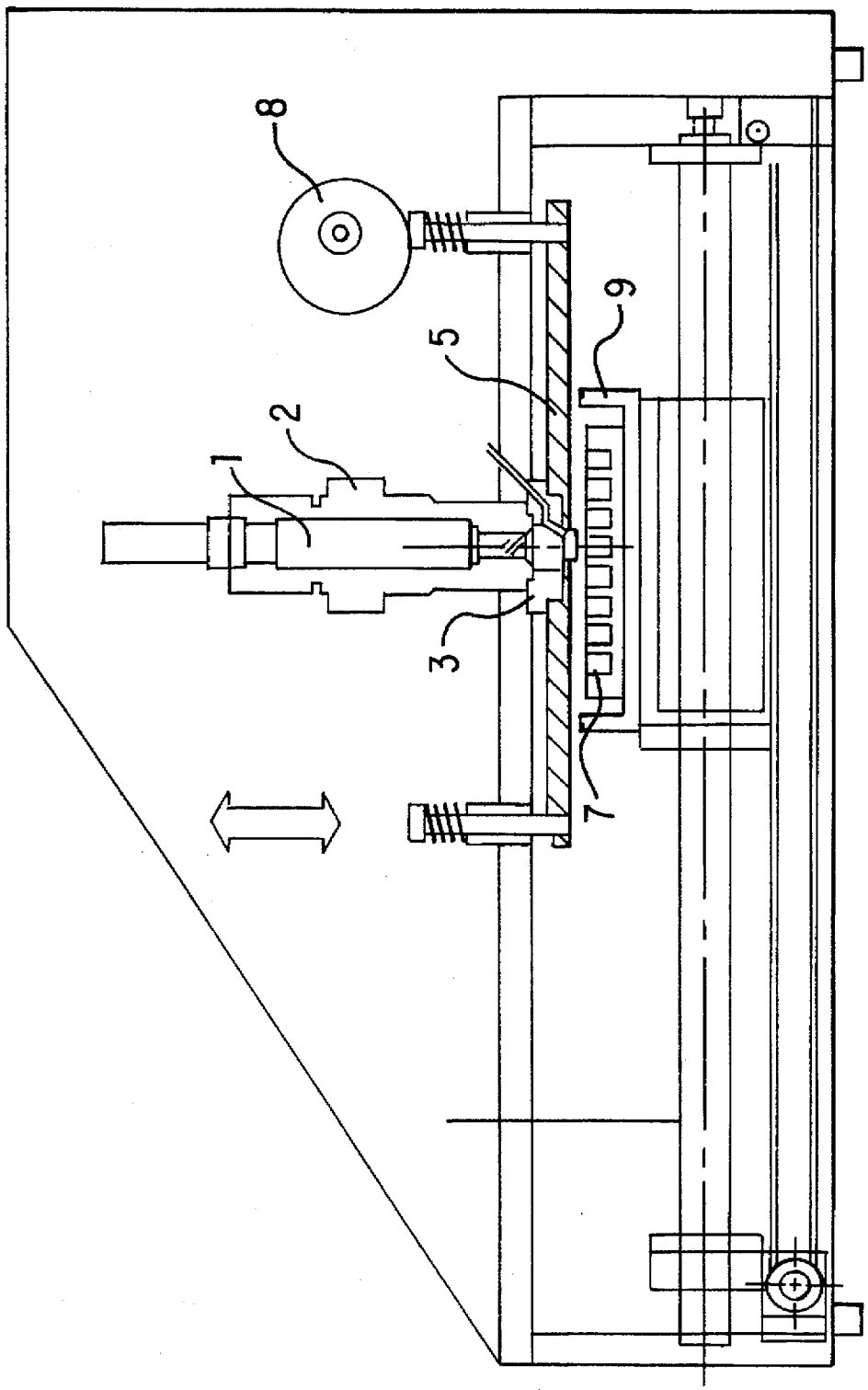
FIG. 2 is a cross-sectional view taken at the movement of a microplate of FIG. 1.
Figure 3:
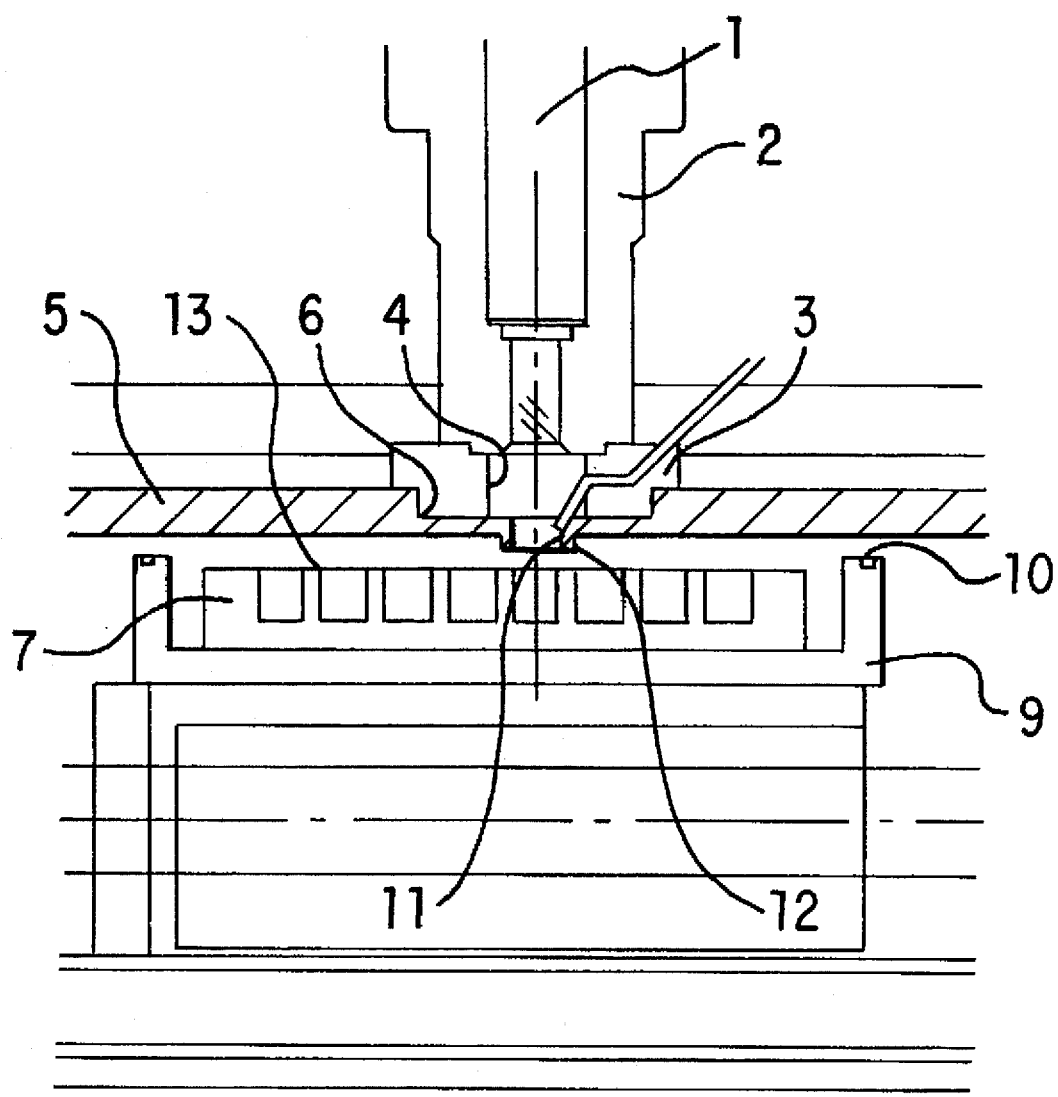
FIG. 3 is an enlarged view of a principal portion of FIG. 2.

Referring to the drawings, a description will be made hereinbelow of a microplate light-obstruction device and a light-emission measuring apparatus using this device according to the present invention. FIG. 1 is a cross-sectional view of the apparatus which is in light-emission measurement, FIG. 2 is a cross-sectional view of the apparatus where a microplate is in movement, and FIG. 3 is an enlarged view of a principal portion thereof.

In FIG. 1, designated at numeral 1 is a well-known photomultiplier serving as a light-emission detecting means, which is fixedly accommodated within a shielding case 2. Further, denoted at numeral 3 is a cylindrical nozzle fixing block for a trigger reagent injector. The cylindrical nozzle fixing block 3 has a through-hole 4 made to be coaxial with the photomultiplier 1, so that a light beam due to the light emission or luminescence passes through this through-hole 4 and then reaches a light-receiving surface of the photomultiplier 1. Basically, the light-receiving surface of the photomultiplier 1 is covered by the shielding case 2 or the like so as to inhibit the reception of light other than the light coming from the through-hole 4 of the nozzle fixing block 3.

This nozzle fixing block 3 is fixed so as not to movable with respect to the photomultiplier 1, and a side surface of a guide hole 6 of a light-obstruction plate 5 is brought into contact with a side surface of the nozzle fixing block 3. The nozzle fixing block 3 is made to slide upwardly at the movement of a microplate 7. Although this portion is fitting-precessed in order to avoid the leakage of light from the external, for the light obstruction it is also possible to envelop or surround it with a bellows or the like from the outside. In addition, it is also appropriate that, instead of the formation of the guide hole 6, the light-obstruction plate 5 and the nozzle fixing block 3 are enveloped with a light-obstruction member such as a bellows for connection.

Moreover, it is possible that the nozzle fixing block 3 and the guide hole 6 of the light-obstruction plate 5 have a cylindrical configuration, and it is also possible that both have an angular configuration to be engaged with each other to prevent mutual revolutions.

The light-obstruction plate 5 is moved up and down through a cam 8 coupled to a motor (not shown) and retreats upwardly at the movement of the microplate 7 as shown in FIG. 2. On the other hand, at measurement the light-obstruction plate 5 moves down to come into tight contact with an outer circumference top surface 10 of a box-type carrier 9 to form a complete black box.

Simultaneously with this, a cylindrical projecting bottom surface 12, which is made around a light-receiving hole 11 open in a bottom portion of the guide hole 6, comes into tight contact with a top surface 13 of a well outer circumference of the microplate 7 which includes a sample, with the result that a black box is established with one well, the light-receiving hole 11 of the light-obstruction plate 5, the nozzle fixing block 3 and the shielding case 2, thus shutting off extremely weak light from other wells to prevent the crosstalk.

The contact portion between the light-obstruction plate 5 and the box-type carrier 9 can easily take a light-obstruction condition in such a manner that an elastic member such as a black urethane-made sponge is set on the outer circumference top surface 10 in the box-type carrier 9 side. The outer circumference top surface 10 of the box-type carrier 9 is made to be higher than the well outer circumference top surface 13 of the microplate 7 accommodated. Further, although the box-type carrier 9 can have any shape as long as it can accommodate the microplate 7, it is desirable that it is designed to fix the microplate 7 accommodated.

Furthermore, designated at numeral 14 is a shaft for shifting the microplate 7 in x and y directions. The box-type carrier 9 includes a sliding bearing at its lower portion and is connected therethrough to the shaft 14. Driven by a timing belt (not shown) coupled to the box-type carrier 9, the box-type carrier 9 is horizontally shifted along the shaft 14 in the x and y directions to successively select and measure given wells. In the ordinary case, at this time the light-obstruction plate 5 stays retreated at the upper side by the cam 8 and does not move. However, in the case of no possibility of the cross contamination, the light-obstruction plate 5 can also slide without retreating at the upper side.

As described above, in the microplate light-obstruction means according to this invention, with only one light-obstruction plate it is possible to shut off the strong light from the external as well as to achieve double light obstruction for the crosstalk prevention with the adjacent wells.

In addition, in the light-emission measuring apparatus according to this invention, because of not establishing the light obstruction of the entire apparatus, the thermal adverse influence from motors and electronic parts within the apparatus is avoidable, a particular microplate is unnecessary and the cross contamination is reducible, thus resulting in a low-cost and general-purpose light-emission measuring apparatus capable of sharply improving its measurement accuracy. It should be understood that the foregoing relates to only preferred embodiments of the present invention, and that it is intended to cover all changes and modifications of the embodiments of the invention herein used for the purposes of the disclosure, which do not constitute departures from the spirit and scope of the invention.

What is claimed is:

1. A microplate light-obstruction device comprising:

a box-type carrier having an open top surface and made to accommodate a microplate comprising a plurality of wells, said box-type carrier being disposed to be movable horizontally; and a light-obstruction plate having a light-receiving hole and disposed above said box-type carrier to be movable vertically, said light-obstruction plate being brought into tight contact with a circumference of said box-type carrier to establish a black box when being moved downwardly, and said light-receiving hole of said light-obstruction plate having a cylindrical projecting bottom surface so that its bottom surface side outer circumference comes into tight contact with a circumference of an opening of a well top surface of said microplate.

2. A microplate light-obstruction device as defined in claim 1, wherein said box-type carrier is made to fix said microplate accommodated.

3. A light-emission measuring apparatus comprising:

a box-type carrier having an open top surface and made to accommodate a microplate comprising a plurality of wells, said box-type carrier being disposed to be movable horizontally;

a light-obstruction plate having a light-receiving hole and disposed above said box-type carrier to be movable vertically, said light-obstruction plate being brought into tight contact with a circumference of said box-type carrier to establish a black box when being moved downwardly, and said light-receiving hole of said light-obstruction plate having a projecting configuration so that its bottom surface side outer circumference comes into tight contact with a circumference of an opening of a well top surface of said microplate, and said light-obstruction plate having a recessed guide hole made around said light-receiving hole in a light-obstruction plate top surface;

a nozzle fixing block having a through-hole made coaxially with respect to said light-receiving hole, said nozzle fixing block being placed above said guide hole so that a nozzle of a trigger reagent injector faces said through-hole; and a light-emission detecting means located above said through-hole, wherein said guide hole of said light-obstruction plate is slidable when said light-obstruction plate moves up and down with respect to said nozzle fixing block.

4. A light-emission measuring apparatus comprising:

a box-type carrier having an open top surface and made to accommodate a microplate comprising a plurality of wells, said box-type carrier being disposed to be movable horizontally;

a light-obstruction plate having a light-receiving hole and disposed above said box-type carrier to be movable vertically, said light-obstruction plate being brought into tight contact with a circumference of said box-type carrier to establish a black box when being moved downwardly, and said light-receiving hole of said light-obstruction plate having a projecting configuration so that its bottom surface side outer circumference comes into tight contact with a circumference of an opening of a well top surface of said microplate;

a nozzle fixing block having a through-hole made coaxially with respect to said light-receiving hole, said nozzle fixing block being placed above said light-receiving hole so that a nozzle of a trigger reagent injector faces said through-hole;

an elastic light-obstruction member provided for envelopment of said light-obstruction plate and said nozzle fixing block so that said light-obstruction plate is movable up and down, to thus shut off light from the external through a gap between said light-receiving hole of said light-obstruction plate and said through-hole of said nozzle fixing block; and a light-emission detecting means located above said through-hole.

5. A light-emission measuring apparatus comprising:

a box-type carrier having an open top surface and made to accommodate a microplate comprising a plurality of wells, said box-type carrier being disposed to be movable horizontally;

a light-obstruction plate having a light-receiving hole and disposed above said box-type carrier to be movable vertically, said light-obstruction plate being brought into tight contact with a circumference of said box-type carrier to establish a black box when being moved downwardly, and said light-receiving hole of said light-obstruction plate having a projecting configuration so that its bottom surface side outer circumference comes into tight contact with a circumference of an opening of a well top surface of said microplate, and said light-obstruction plate having a recessed guide hole made around said light-receiving hole in a light-obstruction plate top surface;

a nozzle fixing block having a through-hole made coaxially with respect to said light-receiving hole, said nozzle fixing block being placed above said guide hole so that a nozzle of a trigger reagent injector faces said through-hole; and an elastic light-obstruction member provided for envelopment of said light-obstruction plate and said nozzle fixing block so that said light-obstruction plate is movable up and down, to thus shut off light from the external through a gap between said guide hole of said light-obstruction plate and said nozzle fixing block; and a light-emission detecting means located above said through-hole, wherein said guide hole of said light-obstruction plate is slidable when said light-obstruction plate moves up and down with respect to said nozzle fixing block.

* * * * *